United States Patent [19]

Sawa

[11] Patent Number: 5,942,508
[45] Date of Patent: Aug. 24, 1999

[54] METHOD FOR SOLUBILIZING PYRIDONECARBOXYLIC ACID SOLUBILIZER THEREOF AND AQUEOUS SOLUTION CONTAINING SOLUBILIZED PYRIDONECARBOXYLIC ACID

[75] Inventor: Shirou Sawa, Kobe, Japan

[73] Assignee: Senju Pharmaceutical Co., Ltd., Osaka, Japan

[21] Appl. No.: 09/017,499

[22] Filed: Feb. 2, 1998

[30] Foreign Application Priority Data

Feb. 4, 1997 [JP] Japan .................................. 9-021807

[51] Int. Cl.⁶ ...................... A61K 31/535; A61K 31/495; A61K 31/445; A61K 31/19
[52] U.S. Cl. ...................... 514/235.8; 514/255; 514/318; 514/570
[58] Field of Search .................... 514/570, 255, 514/255.8, 318

[56] References Cited

U.S. PATENT DOCUMENTS

| | | | |
|---|---|---|---|
| 4,792,552 | 12/1988 | Simonovitch | 514/254 |
| 4,801,584 | 1/1989 | Yokose et al. | 514/183 |
| 4,864,023 | 9/1989 | Yokose et al. | 544/66 |

FOREIGN PATENT DOCUMENTS

| | | |
|---|---|---|
| 0 269 278 | 6/1988 | European Pat. Off. . |
| 2 165 751 | 4/1986 | United Kingdom . |
| 96/38174 | 12/1996 | WIPO . |

OTHER PUBLICATIONS

"The Merck Index 12th Edition", 1996, Merck & Co., Inc., Whitehouse Station, N.J. (US) XP–002065159.

*Primary Examiner*—Raymond Henley, III
*Attorney, Agent, or Firm*—Wenderoth, Lind & Ponack, L.L.P.

[57] ABSTRACT

A method for solubilizing a pyridonecarboxylic acid or a pharmacologically acceptable salt thereof, which comprises adding an arylcarboxylic acid of the formula (I):

$$L^1—R^1COOH \quad (I)$$

wherein $L^1$ is an optionally substituted heterocyclic group or aryl group having not more than 14 carbon atoms, and $R^1$ is an optionally substituted alkyl group having not more than 4 carbon atoms or a single bond, to the pyridonecarboxylic acid or the pharmacologically acceptable salt thereof, a solubilizer thereof and an aqueous solution containing a solubilized pyridonecarboxylic acid. According to the solubilization method of the present invention, the solubility of pyridonecarboxylic acid compounds and salts thereof at near physiological pH can be increased, thereby making the production of an aqueous solution to be used as an eye drop, nasal drop, ear drop and the like possible.

6 Claims, No Drawings

METHOD FOR SOLUBILIZING PYRIDONECARBOXYLIC ACID SOLUBILIZER THEREOF AND AQUEOUS SOLUTION CONTAINING SOLUBILIZED PYRIDONECARBOXYLIC ACID

TECHNICAL FIELD OF THE INVENTION

The present invention relates to a method for solubilizing a pyridonecarboxylic acid, which is an amphoteric compound and which has an antibacterial activity, or a pharmacologically acceptable salt thereof, a solubilizer thereof and an aqueous solution containing a solubilized pyridonecarboxylic acid.

BACKGROUND OF THE INVENTION

Pyridonecarboxylic acid and pharmacologically acceptable salts thereof have been known to be extremely superior synthetic antibacterial agents. However, since said pyridonecarboxylic acid has carboxylic acid and the dihydropyridine skeleton in a molecule, forming a zwitterion, it shows strikingly low solubility in water at a physiological pH, i.e., neutral range. This imposes a problem that an aqueous solution containing pyridonecarboxylic acid or a pharmacologically acceptable salt thereof cannot be formulated into a pharmaceutical preparation at a neutral pH.

Hardly soluble pyridonecarboxylic acid and a pharmacologically acceptable salt thereof are solubilized by, for example, adding an inorganic acid to pyridonecarboxylic lactate (U.S. Pat. No. 4,705,789, U.S. Pat. No. 4,808,583, U.S. Pat. No. 4,808,585), or adding a base in excess to pyridonecarboxylic acid (U.S. Pat. No. 4,772,605), or adding a metal compound comprising aluminum, magnesium or zinc to pyridonecarboxylic acid or a salt thereof (Japanese Patent Unexamined Publication No. 188626/1988). The aqueous preparations thus obtained are associated with variations in pH which are caused by the solubilizer added, and the toxicity of the solubilizer itself which may cause a local irritation and the like, possibly leading to unexpected disorders.

Thus, there has not been provided an aqueous preparation containing solubilized pyridonecarboxylic acid, which is safe and useful at a physiological pH, i.e., about neutral pH.

SUMMARY OF THE INVENTION

It is therefore an object of the present invention to provide a method for solubilizing a pyridonecarboxylic acid and a pharmacologically acceptable salt thereof.

Another object of the present invention is to provide a solubilizer of a pyridonecarboxylic acid and a pharmacologically acceptable salt thereof, which contains an arylcarboxylic acid as an active ingredient.

Yet another object of the present invention is to provide an aqueous solution containing a solubilized pyridonecarboxylic acid and an arylcarboxylic acid.

A further object of the present invention is to provide an aqueous solution containing a pyridonecarboxylic acid or a pharmacologically acceptable salt thereof at a high concentration.

According to the present invention, it has now been found that the addition of an arylcarboxylic acid to a pyridonecarboxylic acid or a pharmacologically acceptable salt thereof leads to successful solubilization thereof at around a physiological pH.

Thus, the present invention provides the following.

(1) A method for solubilizing a pyridonecarboxylic acid or a pharmacologically acceptable salt thereof, which comprises adding an arylcarboxylic acid of the formula (I):

$$L^1-R^1\ COOH \tag{I}$$

wherein
$L^1$ is an optionally substituted heterocyclic group or aryl group having not more than 14 carbon atoms; and
$R^1$ is an optionally substituted alkyl group having not more than 4 carbon atoms or a single bond,
to the pyridonecarboxylic acid or the pharmacologically acceptable salt thereof.

(2) The method of (1) above, wherein the arylcarboxylic acid is at least one compound selected from the group consisting of pranoprofen, ibuprofen, bromfenac, 2-naphthoic acid, 2-naphthylacetic acid and 2-naphthoxyacetic acid.

(3) The method of (1) above, wherein the pyridonecarboxylic acid is of the formula (II):

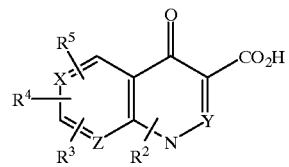

wherein
X, Y and Z are each a nitrogen atom or an optionally substituted CH; and
$R^2$, $R^3$, $R^4$ and $R^5$ may be the same or different and each is a hydrogen atom, a halogen, a carboxyl group, an optionally substituted lower alkyl group, an optionally substituted cycloalkyl group, an optionally substituted lower acyl group, an optionally substituted aryl group or an optionally substituted heterocyclic group,
wherein two or more groups from among Z, $R^2$, $R^3$, $R^4$ and $R^5$ may form a 4- to 7-membered ring.

(4) The method of (3) above, wherein the pyridonecarboxylic acid is at least one compound selected from the group consisting of lomefloxacin, norfloxacin, enoxacin, ofloxacin, ciprofloxacin, tosufloxacin, fleroxacin, cinoxacin, levofloxacin and sparfloxacin.

(5) The method of any one of the above (1) to (4), wherein the arylcarboxylic acid is added in a proportion of 0.001–50 parts by weight per part by weight of the pyridonecarboxylic acid.

(6) A solubilizer of a pyridonecarboxylic acid or a pharmacologically acceptable salt thereof, which comprises, as an active ingredient, an arylcarboxylic acid of the formula (I):

$$L^1-R^1\ COOH \tag{I}$$

wherein
$L^1$ is an optionally substituted heterocyclic group or aryl group having not more than 14 carbon atoms; and
$R^1$ is an optionally substituted alkyl group having not more than 4 carbon atoms or a single bond.

(7) The solubilizer of (6) above, wherein the arylcarboxylic acid is at least one compound selected from the group consisting of pranoprofen, ibuprofen, bromfenac, 2-naphthoic acid, 2-naphthylacetic acid and 2-naphthoxyacetic acid.

(8) The solubilizer of (6) above, wherein the pyridonecarboxylic acid is of the formula (II):

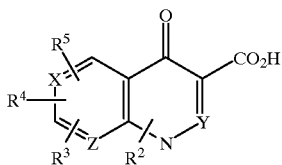

(II)

wherein
X, Y and Z are each a nitrogen atom or an optionally substituted CH; and
$R^2$, $R^3$, $R^4$ and $R^5$ may be the same or different and each is a hydrogen atom, a halogen, a carboxyl group, an optionally substituted lower alkyl group, an optionally substituted cycloalkyl group, an optionally substituted lower acyl group, an optionally substituted aryl group or an optionally substituted heterocyclic group,
wherein two or more groups from among Z, $R^2$, $R^3$, $R^4$ and $R^5$ may form a 4- to 7-membered ring.

(9) The solubilizer of (8) above, wherein the pyridonecarboxylic acid is at least one compound selected from the group consisting of lomefloxacin, norfloxacin, enoxacin, ofloxacin, ciprofloxacin, tosufloxacin, fleroxacin, cinoxacin, levofloxacin and sparfloxacin.

(10) The solubilizer of any one of the above (6) to (9), wherein the arylcarboxylic acid is added in a proportion of 0.001–10 parts by weight per part by weight of the pyridonecarboxylic acid.

(11) An aqueous solution comprising a pyridonecarboxylic acid or a pharmacologically acceptable salt thereof solubilized by the method of (1) above, and an arylcarboxylic acid of the formula (I):

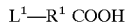

$L^1$—$R^1$ COOH (I)

wherein
$L^1$ is an optionally substituted heterocyclic group or aryl group having not more than 14 carbon atoms; and
$R^1$ is an optionally substituted alkyl group having not more than 4 carbon atoms or a single bond.

(12) The solution of (11) above, wherein the arylcarboxylic acid is at least one compound selected from the group consisting of pranoprofen, ibuprofen, bromfenac, 2-naphthoic acid, 2-naphthylacetic acid and 2-naphthoxyacetic acid.

(13) The solution of (11) above, wherein the pyridonecarboxylic acid is of the formula (II):

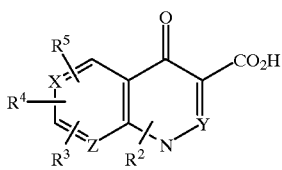

(II)

wherein
X, Y and Z are each a nitrogen atom or an optionally substituted CH; and
$R^2$, $R^3$, $R^4$ and $R^5$ may be the same or different and each is a hydrogen atom, a halogen, a carboxyl group, an optionally substituted lower alkyl group, an optionally substituted cycloalkyl group, an optionally substituted lower acyl group, an optionally substituted aryl group or an optionally substituted heterocyclic group,
wherein two or more groups from among Z, $R^2$, $R^3$, $R^4$ and $R^5$ may form a 4- to 7-membered ring.

(14) The solution of (13) above, wherein the pyridonecarboxylic acid is at least one compound selected from the group consisting of lomefloxacin, norfloxacin, enoxacin, ofloxacin, ciprofloxacin, tosufloxacin, fleroxacin, cinoxacin, levofloxacin and sparfloxacin.

(15) The solution of any one of the above (11) to (14), which is an eye drop.

(16) The solution of any one of the above (11) to (14), which is a nasal drop.

(17) The solution of any one of the above (11) to (14), which is an ear drop.

(18) An aqueous solution comprising at least a pyridonecarboxylic acid or a pharmacologically acceptable salt thereof in a concentration of 0.2–5.0 (w/v)%.

(19) The solution of (18) above, wherein the pyridonecarboxylic acid is of the formula (II):

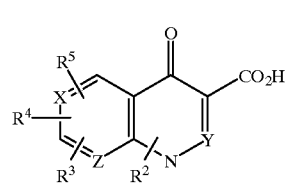

(II)

wherein
X, Y and Z are each a nitrogen atom or an optionally substituted CH; and
$R^2$, $R^3$, $R^4$ and $R^5$ may be the same or different and each is a hydrogen atom, a halogen, a carboxyl group, an optionally substituted lower alkyl group, an optionally substituted cycloalkyl group, an optionally substituted lower acyl group, an optionally substituted aryl group or an optionally substituted heterocyclic group,
wherein two or more groups from among Z, $R^2$, $R^3$, $R^4$ and $R^5$ may form a 4- to 7-membered ring.

(20) The solution of (18) above, wherein the pyridonecarboxylic acid is at least one compound selected from the group consisting of lomefloxacin, norfloxacin, enoxacin, ofloxacin, ciprofloxacin, tosufloxacin, fleroxacin, cinoxacin, levofloxacin and sparfloxacin.

DETAILED DESCRIPTION OF THE INVENTION

The solubilizing method of the present invention comprises the addition of a solubilizer containing an arylcarboxylic acid as an active ingredient to a pyridonecarboxylic acid, which is an amphoteric compound and which has an antibacterial activity, or a pharmacologically acceptable salt thereof. For example, an arylcarboxylic acid is added to a pyridonecarboxylic acid or a pharmacologically acceptable salt thereof.

To be specific, the arylcarboxylic acid is dissolved in water and adjusted to pH 3 and added. Thereafter, the pH is adjusted to 3.5–8.5, preferably 6–8.

Said arylcarboxylic acid has the following formula (I)

$L^1$—$R^1$ COOH (I)

wherein
$L^1$ is an optionally substituted heterocyclic group or aryl group having not more than 14 carbon atoms; and $R^1$ is an optionally substituted alkyl group having not more than 4 carbon atoms or a single bond,
and can be used without any particular limitation.

The heterocyclic group of the optionally substituted heterocyclic group having not more than 14 carbon atoms may contain, as the atom constituting the ring, at least one hetero atom selected from the group consisting of nitrogen atom, sulfur atom and oxygen atom, besides carbon atom, and may be a saturated or unsaturated heteromonocyclic or heteropolycyclic group.

Preferable heterocyclic groups are the following:

3- to 6-membered unsaturated heteromonocyclic group having 1 to 4 nitrogen atoms, such as pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl and the like), tetrazolyl (e.g., 1H-tetrazolyl, 2H-tetrazolyl and the like), triazinyl (e.g., 1,2,4-triazinyl and the like), and the like;

3- to 7-membered saturated heteromonocyclic group having 1 to 4 nitrogen atoms, such as pyrrolidinyl, imidazolidinyl, piperidinyl, piperazinyl, homopiperazinyl and the like;

saturated heteropolycyclic group having 1 to 4 nitrogen atoms, such as quinuclidinyl and the like;

unsaturated heteropolycyclic group having 1 to 5 nitrogen atoms, such as indolyl, isoindolyl, 3H-indolyl, indolizinyl, benzoimidazolyl, quinolyl, isoquinolyl, indazolyl, phthalazinyl, naphthyridinyl, quinoxalinyl, quinazolinyl, cinnolinyl, benzotriazolyl, tetrazolopyridazinyl (e.g., tetrazolo[1,5-b]pyridazinyl and the like), pteridinyl, carbazolyl, phenanthrinidyl, acridinyl, perimidyl, and the like;

3- to 6-membered unsaturated heteromonocyclic group having 1 to 3 nitrogen atoms and 1 or 2 oxygen atoms, such as oxazolyl, isooxazolyl, oxadiazolyl (e.g., 1,2,4-oxadiazolyl, 1,3,4-oxadiazolyl, 1,2,5-oxadiazolyl and the like), and the like;

3- to 6-membered saturated heteromonocyclic group having 1 to 3 nitrogen atoms and 1 or 2 oxygen atoms, such as morpholinyl, sydnolyl, and the like;

unsaturated condensed heterocyclic group having 1 to 3 nitrogen atoms and 1 or 2 oxygen atoms, such as benzofurazanyl, benzoxazolyl, benzoxazinyl, benzoxadiazolyl, and the like;

3- to 6-membered unsaturated condensed heterocyclic group having 1 to 3 nitrogen atoms and 1 or 2 sulfur atoms, such as thiazolyl, isothiazolyl, thiadiazolyl (e.g., 1,2,4-thiadiazolyl, 1,3,4-thiadiazolyl, 1,2,5-thiadiazolyl and the like), and the like;

3- to 6-membered saturated heteromonocyclic group having 1 to 3 nitrogen atoms and 1 or 2 sulfur atoms, such as thiazolidinyl and the like;

unsaturated condensed heterocyclic group having 1 to 3 nitrogen atoms and 1 or 2 sulfur atoms, such as benzothiazolyl, benzothiadiazolyl, and the like;

3- to 6-membered unsaturated heteromonocyclic group having 1 oxygen atom, such as furyl, pyranyl and the like;

3- to 6-membered unsaturated heteromonocyclic group having 1 or 2 sulfur atoms, such as thienyl, dihydrothienyl, and the like;

unsaturated condensed heterocyclic group having 1 or 2 sulfur atoms, such as benzothienyl and the like; and the like.

The aryl moiety of the optionally substituted aryl group having not more than 14 carbon atoms may be, for example, phenyl, naphthyl and the like, with preference given to naphthyl.

Said heterocyclic group and aryl group are optionally substituted by one or more substituents selected from the group consisting of aliphatic alkyl group, aromatic alkyl group, aliphatic carboxylic acid group, aromatic carboxylic acid group, aliphatic carboxylate group, aromatic carboxylate group, aliphatic ether group, aromatic ether group, aliphatic alcohol group, aromatic alcohol group, aliphatic aldehyde group, aromatic aldehyde group, aliphatic amino group, aromatic amino group, which are optionally substituted by hydroxyl group, halogen atom or halogen atom.

The alkyl moiety of the optionally substituted alkyl group having not more than 4 carbon atoms may be, for example, a linear or branched one such as methyl, ethyl, propyl, isopropyl, butyl, isobutyl, tert-butyl and the like.

Examples of the arylcarboxylic acid include naphthoic acid-related compounds, salicylic acid-related compounds, phenylacetic acid-related compounds, pyrazolone-related compounds, anthranilic acid-related compounds, indoleacetic acid-related compounds, fenclozic acid-related compounds and salts thereof and the like.

Examples of the naphthoic acid-related compounds include 2-naphthoic acid, 2-naphthylacetic acid, 2-naphthoxyacetic acid and the like.

Examples of the salicylic acid-related compounds include salicylic acid, aspirin, flufenisal, ethenzamide, benorylate and the like.

Examples of the phenylacetic acid-related compounds include ibufenac, alclofenac, flurbiprofen, ketoprofen, naproxen, ibuprofen, bromfenac, pranoprofen, namoxylate, fenoprofen and the like.

Examples of the pyrazolone-related compounds include aminopyrine, phenylbutazone, azapropazone, cinopentazone and the like.

Examples of the anthranilic acid-related compounds include mefenamic acid, niflumic acid, diclofenac, metiazinic acid, protizinic acid, clonixin, flufenamic acid, ketoprofen and the like.

Examples of the indoleacetic acid-related compounds include indometacin, intrazole and the like.

The pyridonecarboxylic acid to be used for the solubilizing method of the present invention has a carboxyl group at the 3-position of the pyridine skeleton or pyridazine skeleton and an oxo group at the 4-position thereof.

The pyridonecarboxylic acid in the present specification has a solubility in water which corresponds to the solubility of from "somewhat insoluble" to "sparingly soluble" as defined in Japan Pharmacopoeia, 12th Edition, Explanation (1991), Hirokawashoten, Tokyo, p. A-45, General Notices 24, Description, or from "sparingly soluble" to "practically insoluble" as defined in International Pharmacopoeia III.

Preferable pyridonecarboxylic acid has the following formula (II)

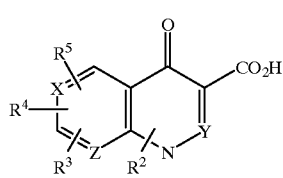

(II)

wherein
X, Y and Z are each a nitrogen atom or an optionally substituted CH;

$R^2$, $R^3$, $R^4$ and $R^5$ may be the same or different and each is a hydrogen atom, a halogen, a carboxyl group, an optionally substituted lower alkyl group, an optionally substituted cycloalkyl group, an optionally substituted lower acyl group, an optionally substituted aryl group or an optionally substituted heterocyclic group, wherein two or more groups from among Z, $R^2$, $R^3$, $R^4$ and $R^5$ may form a 4- to 7-membered ring.

The lower alkyl of the "optionally substituted lower alkyl group" has 1 to 6 carbon atoms, and is exemplified by a linear or branched one such as methyl, ethyl, propyl, isopropyl, butyl, isobutyl, tert-butyl, pentyl, isopentyl, neopentyl, tert-pentyl, hexyl, isohexyl, neohexyl and the like.

The cycloalkyl of the "optionally substituted cycloalkyl group" has 3 to 9 carbon atoms, and is exemplified by cyclopropyl, cyclobutyl, cyclopentyl, cyclohexyl, cycloheptyl and the like.

The substituents of the above-mentioned lower alkyl group and cycloalkyl group include lower alkyl group, halogen and the like.

The lower acyl moiety of the optionally substituted lower acyl group may be, for example, formyl group, acetyl group, propionyl group, butyryl group, isobutyryl group, valeryl group, benzoyl group, naphthoyl group, toluoyl group, salicyloyl group and the like.

The above-mentioned acyl moiety may be substituted by suitable substituents which may be the same or different, such as lower alkyl (e.g., methyl, ethyl, propyl etc.);

lower alkoxy (e.g., methoxy, ethoxy, propoxy etc.);

lower alkylthio (e.g., methylthio, ethylthio etc.);

lower alkylamino (e.g., methylamino, ethylamino, propylamino and the like);

cyclo(lower)alkyl such as cyclo($C_3$–$C_6$)alkyl (e.g., cyclopentyl, cyclohexyl and the like);

cyclo(lower)alkenyl such as cyclo($C_3$–$C_6$)alkenyl (e.g., cycloxenyl, cyclohexadienyl and the like);

halogen (e.g., fluorine, chlorine, bromine, iodine);

amino, amino protecting group, hydroxy, protected hydroxy, cyano, nitro, carboxy, protected carboxy, sulfo, sulfamoyl, imino, oxo;

amino(lower)alkyl (e.g., aminomethyl, aminoethyl and the like), carbamoyloxy, hydroxy(lower)alkyl (e.g., hydroxymethyl, 1- or 2-hydroxyethyl, 1- or 2- or 3-hydroxypropyl and the like); and the like.

The aryl moiety and heterocyclic moiety of the optionally substituted aryl group and optionally substituted heterocyclic group are exemplified by those mentioned above, and the substituents of said aryl group and heterocyclic group are also exemplified by those mentioned above.

The 4- to 7-membered heterocyclic group formed by two or more optional groups from among Z, $R^2$, $R^3$, $R^4$ and $R^5$ may be, for example, thienyl group, furyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, pyridyl group, pyrazinyl group, pyrimidinyl group, pyridazinyl group, triazinyl group, dithiazolyl group, dioxolanyl group, dithiolyl group, pyrrolidinyl group, thiaziadinyl group, dithiaziadinyl group, morpholinyl group, oxazinyl group, thiazinyl group, piperazinyl group, piperidinyl group, pyranyl group, thiopyranyl group and the like.

Examples of the pyridonecarboxylic acid include enoxacin: [1-ethyl-6-fluoro-1,4-dihydro-4-oxo-7-(1-piperazinyl)-1,8-naphthyridine-3-carboxylic acid], ofloxacin: [(±)-9-fluoro-2,3-dihydro-3-methyl-10-(4-methyl-1-piperazinyl)-7-oxo-7H-[1,2,3-de]-1,4-benzoxazine-6-carboxylic acid], cinoxacin: [1-ethyl-1,4-dihydro-4-oxo-[1,3]-dioxolo[4,5-g]cinnoline-3-carboxylic acid], ciprofloxacin: [1-cyclopropyl-6-fluoro-1,4-dihydro-4-oxo-7-(1-piperazinyl)-3-quinolinecarboxylic acid], sparfloxacin: [5-amino-1-cyclopropyl-7-(cis-3,5-dimethyl-1-piperazinyl)-6,8-difluoro-1,4-dihydro-4-oxoquinoline-3-carboxylic acid], tosufloxacin: [(±)-7-(3-amino-1-pyrrolidinyl)-1-(2,4-difluorophenyl)-6-fluoro-1,4-dihydro-4-oxo-1-naphthyridine-3-carboxylic acid], norfloxacin: [1-ethyl-6-fluoro-1,4-dihydro-4-oxo-7-(1-piperazinyl)-3-quinolinecarboxylic acid], fleroxacin: [6,8-difluoro-1-(2-fluoroethyl)-1,4-dihydro-7-(4-methyl-1-piperazinyl)-4-oxo-3-quinolinecarboxylic acid], levofloxacin: [(−)-(S)-9-fluoro-2,3-dihydro-3-methyl-10-(4-methyl-1-piperazinyl)-7-oxo-7H-pyrido[1,2,3-de][1,4]benzoxazine-6-carboxylic acid], lomefloxacin: [1-ethyl-6,8-difluoro-1,4-dihydro-7-(3-methyl-1-piperazinyl)-4-oxo-3-quinolinecarboxylic acid], 5,8-dihydro-8-ethyl-2-(1-piperazinyl)-5-oxopyrido[2,3-d]pyrimidinecarboxylic acid, 7-(3-amino-1-pyrrolidinyl)-1-ethyl-6-fluoro-1,4-dihydro-4-oxo-1,8-naphthyridine-3-carboxylic acid, 7-(3-amino-1-pyrrolidinyl)-1-cyclopropyl-6-fluoro-1,4-dihydro-4-oxo-1,8-naphthyridine-3-carboxylic acid, 1-cyclopropyl-6-fluoro-7-(3-methylamino-1-pyrrolidinyl)-1,4-dihydro-4-oxo-1,8-naphthyridine-3-carboxylic acid, 7-(3-amino-3-methyl-1-pyrrolidinyl)-1-cyclopropyl-6-fluoro-1,4-dihydro-4-oxo-1,8-naphthyridine-3-carboxylic acid and the like, salts thereof and the like.

The pharmacologically acceptable salts of pyridonecarboxylic acid include, for example, acid addition salts with inorganic acids such as hydrochloric acid, sulfuric acid, phosphoric acid and the like, organic acids such as acetic acid, lactic acid, succinic acid, methanesulfonic acid, maleic acid, malonic acid, gluconic acid and the like, and amino acids such as aspartic acid, glutamic acid and the like; metal salts such as sodium salt, potassium salt and the like; and the like.

The amount of the arylcarboxylic acid to be added to the pyridonecarboxylic acid or a pharmacologically acceptable salt thereof is preferably about 0.001–10 parts by weight per part by weight of the pyridonecarboxylic acid or pharmacologically acceptable salt thereof.

The solubilizer of the pyridonecarboxylic acid and a pharmacologically acceptable salt thereof contains arylcarboxylic acid as an active ingredient in almost the same amount as mentioned above.

The solvent to be used for the aqueous solution of the present invention may be, for example, purified water, particularly distilled water for injection. The concentration of the active ingredient of the aqueous solution, i.e. pyridonecarboxylic acid, can be markedly increased by arylcarboxylic acid, preferably to 0.2–5.0 (w/v)%.

The arylcarboxylic acid to be used for the aqueous solution of the present invention may be those mentioned above.

Said aqueous solution may contain various additives as appropriate, such as buffer, isotonizing agent, solubilizer, antiseptic, thickener, chelating agent, aromatic and the like.

Examples of the buffer include phosphate buffer, borate buffer, citrate buffer, tartrate buffer, acetate buffer, amino acid and the like.

Examples of the isotonizing agent include sugars such as sorbitol, glucose, mannitol and the like, polyhydric alcohols such as glycerol, propylene glycol and the like, salts such as sodium chloride and the like, and the like.

Examples of the solubilizer include non-ionic surfactants such as polyoxyethylenesorbitane monoolate, polyoxyethyleneoxystearic acid triglyceride, polyethylene glycol, polyoxyethylene hydrogenated castor oil and the like, and the like.

Examples of the antiseptic include quaternary ammonium salts such as benzalkonium chloride, benzethonium chloride, cetylpyridinium chloride and the like, p-hydroxybenzoates such as methyl p-hydroxybenzoate, ethyl p-hydroxybenzoate, propyl p-hydroxybenzoate, butyl p-hydroxybenzoate and the like, benzyl alcohol, phenetyl alcohol, sorbic acid, salts thereof, thimerosal, chlorobutanol, sodium dehydroacetate and the like.

Examples of the thickener include polyvinylpyrrolidone, hydroxyethylcellulose, hydroxypropylcellulose, methylcellulose, hydroxypropylmethylcellulose, carboxymethylcellulose, salts thereof and the like.

Examples of the chelating agent include sodium edetate, citric acid, salt thereof and the like.

Examples of the aromatic include 1-menthol, borneol, camphor, eucalyptus oil and the like.

The aqueous solution of the present invention is used as an eye drop, nasal drop or ear drop. When it is used as an eye drop, its pH is generally adjusted to about 3.5–8.5, preferably about 6–8, when it is used as a nasal drop, its pH is generally adjusted to about 3.5–8.5, preferably about 6–8, and when it is used as an ear drop, its pH is generally adjusted to about 3.5–8.5, preferably about 6–8.

While the method for producing the aqueous solution of the present invention varies depending on the kind of a desired solution, a known method can be used to produce such aqueous solution.

When the aqueous solution of the present invention is used as an eye drop, for example, the dose thereof need only be sufficient to effectively suppress inflammation in the eye, and may vary according to symptoms, the kind of inflammation, the patients in need of said solution and the like. A typical dose is 20–200 $\mu$L, preferably 50–100 $\mu$L, which may be administered 1 to 12 times a day.

The present invention is described in more detail by way of Examples and Experimental Examples, which should not be construed as limiting the invention.

Experimental Example 1: Effect of arylcarboxylic acid on solubility of pyridonecarboxylic acid - 1

To a 0.1% aqueous sodium dihydrogenphosphate solution (100 ml) containing pranoprofen, ibuprofen or bromfenac was added norfloxacin or enoxacin in excess, and the pH thereof was adjusted to 7–8 with hydrochloric acid or sodium hydroxide. The mixture was shaken for one week at 25° C. and filtered through a 0.45 $\mu$m membrane filter, which was followed by the determination of a norfloxacin or enoxacin content by high performance liquid chromatography. The results are shown in Table 1.

TABLE 1

|  | solubility (%) | | | |
| --- | --- | --- | --- | --- |
|  | norfloxacin | | enoxacin | |
|  | pH 7 | pH 8 | pH 7 | pH 8 |
| without addition | 0.040 | 0.036 | 0.026 | 0.025 |
| pranoprofen added | 0.181 | 0.081 | 0.078 | 0.063 |
| ibuprofen added | 0.043 | 0.042 | 0.030 | 0.028 |
| bromfenac added | 0.041 | 0.054 | 0.032 | 0.035 |

Experimental Example 2: Effect of arylcarboxylic acid on solubility of pyridonecarboxylic acid - 2

To a 0.1% aqueous sodium dihydrogenphosphate solution (100 ml) containing 2-naphthoic acid, 2-naphthylacetic acid or 2-naphthoxyacetic acid was added norfloxacin or enoxacin in excess, and the pH thereof was adjusted to 8–9 with hydrochloric acid or sodium hydroxide. The mixture was shaken for one week at 25° C. and filtered through a 0.45 $\mu$m membrane filter, which was followed by the determination of a norfloxacin or enoxacin content by high performance liquid chromatography. The results are shown in Table 2.

TABLE 2

|  | solubility (%) | | | |
| --- | --- | --- | --- | --- |
|  | norfloxacin | | enoxacin | |
|  | pH 8 | pH 9 | pH 8 | pH 9 |
| without addition | 0.036 | 0.106 | 0.025 | 0.071 |
| 2-naphthoic acid added | 0.092 | 0.159 | 0.054 | 0.119 |
| 2-naphthylacetic acid added | 0.058 | 0.206 | 0.042 | 0.083 |
| 2-naphthoxyacetic acid added | 0.075 | 0.160 | 0.047 | 0.099 |

Experimental Example 3: Effect of arylcarboxylic acid on solubility of pyridonecarboxylic acid - 3

To a 0.1% aqueous sodium dihydrogenphosphate solution (100 ml) containing pranoprofen, ibuprofen, diclofenac, bromfenac, 2-naphthoic acid, 2-naphthylacetic acid or 2-naphthoxyacetic acid was added lomefloxacin in excess, and the pH thereof was adjusted to 8–9 with hydrochloric acid or sodium hydroxide. The mixture was shaken for one week at 25° C. and filtered through a 0.45 $\mu$m membrane filter, which was followed by the determination of a lomefloxacin content by high performance liquid chromatography. The results are shown in Table 3.

TABLE 3

|  | solubility (%) lomefloxacin | |
| --- | --- | --- |
|  | pH 8 | pH 9 |
| without addition | 0.118 | 0.300 |
| pranoprofen added | 0.214 | — |
| ibuprofen added | — | 0.350 |
| diclofenac added | 0.139 | 0.333 |
| bromfenac added | — | 0.470 |
| 2-naphthoic acid added | 0.230 | — |
| 2-naphthylacetic acid added | 0.180 | — |
| 2-naphthoxyacetic acid added | 0.204 | — |

As is evident from the results shown in Tables 1 to 3, the addition of at least one member selected from the group consisting of arylcarboxylic acid compounds such as pranoprofen, ibuprofen, diclofenac, bromfenac, 2-naphthoic acid, 2-naphthylacetic acid and 2-naphthoxyacetic acid and the like increased the solubility of a pyridonecarboxylic acid compound, such as norfloxacin, enoxacin, lomefloxacin and the like, and salts thereof, by about 1.5–3 times.

Eye drops, nasal drops and ear drops having the following formulations were prepared. Neither of them showed precipitation of crystals after preservation for 4 days at room temperature. The solubility of norfloxacin in 0.1% phosphate buffer (pH 8) and 1.6% borate buffer (pH 7) was 0.036% and 0.039%, respectively; the solubility of enoxacin in 0.1% phosphate buffer (pH 7) and 1.6% borate buffer (pH 6) was 0.028% and 0.17%, respectively; and the solubility of ofloxacin in physiological saline adjusted to pH 7 with phosphoric acid was 0.5%.

EXAMPLE 1

An eye drop having the following formulation was prepared.

| | |
|---|---|
| norfloxacin | 0.04 g |
| bromfenac sodium | 0.4 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 8) |

EXAMPLE 2

An eye drop having the following formulation was prepared.

| | |
|---|---|
| norfloxacin | 0.05 g |
| 2-naphthylacetic acid | 0.3 g |
| boric acid | 1.6 g |
| hydrochloric acid | appropriate amount |
| sodium hydroxide | appropriate amount |
| sterile purified water | appropriate amount |
| total amount | 100 ml (pH 7) |

EXAMPLE 3

An ear drop having the following formulation was prepared.

| | |
|---|---|
| enoxacin | 0.03 g |
| ibuprofen | 0.5 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 7) |

EXAMPLE 4

An eye drop having the following formulation was prepared.

| | |
|---|---|
| enoxacin | 0.25 g |
| 2-naphthoic acid | 0.2 g |
| boric acid | 1.6 g |
| hydrochloric acid | appropriate amount |
| sodium hydroxide | appropriate amount |
| sterile purified amount | appropriate amount |
| total amount | 100 ml (pH 6) |

EXAMPLE 5

A nasal drop having the following formulation was prepared.

| | |
|---|---|
| ofloxacin | 0.8 g |
| 2-naphthoic acid | 0.1 g |
| phosphoric acid | 0.1 g |
| sodium chloride | 0.9 g |
| hydrochloric acid | appropriate amount |
| sodium hydroxide | appropriate amount |
| sterile purified water | appropriate amount |
| total amount | 100 ml (pH 7) |

EXAMPLE 6

An ear drop having the following formulation was prepared.

| | |
|---|---|
| norfloxacin | 0.04 g |
| bromfenac sodium | 0.4 g |
| naphazoline hydrochloride | 0.003 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 8) |

EXAMPLE 7

An ear drop having the following formulation was prepared.

| | |
|---|---|
| norfloxacin | 0.04 g |
| bromfenac sodium | 0.4 g |
| chlorpheniramine maleate | 0.03 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 8) |

EXAMPLE 8

An eye drop having the following formulation was prepared.

| | |
|---|---|
| norfloxacin | 0.04 g |
| bromfenac sodium | 0.4 g |
| pyridoxine hydrochloride | 0.1 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 8) |

EXAMPLE 9

An eye drop having the following formulation was prepared.

| | |
|---|---|
| norfloxacin | 0.05 g |
| 2-naphthylacetic acid | 0.3 g |
| naphazoline hydrochloride | 0.003 g |
| boric acid | 1.6 g |

-continued

| | |
|---|---|
| hydrochloric acid | appropriate amount |
| sodium hydroxide | appropriate amount |
| sterile purified water | appropriate amount |
| total amount | 100 ml (pH 7) |

EXAMPLE 10

An eye drop having the following formulation was prepared.

| | |
|---|---|
| norfloxacin | 0.05 g |
| 2-naphthylacetic acid | 0.3 g |
| chlorpheniramine maleate | 0.003 g |
| boric acid | 1.6 g |
| hydrochloric acid | appropriate amount |
| sodium hydroxide | appropriate amount |
| sterile purified water | appropriate amount |
| total amount | 100 ml (pH 7) |

EXAMPLE 11

An eye drop having the following formulation was prepared.

| | |
|---|---|
| norfloxacin | 0.05 g |
| 2-naphthylacetic acid | 0.3 g |
| pyridoxine hydrochloride | 0.1 g |
| boric acid | 1.6 g |
| hydrochloric acid | appropriate amount |
| sodium hydroxide | appropriate amount |
| sterile purified water | appropriate amount |
| total amount | 100 ml (pH 7) |

EXAMPLE 12

A nasal drop having the following formulation was prepared.

| | |
|---|---|
| enoxacin | 0.03 g |
| ibuprofen | 0.5 g |
| naphazoline hydrochloride | 0.003 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 7) |

EXAMPLE 13

An eye drop having the following formulation was prepared.

| | |
|---|---|
| enoxacin | 0.03 g |
| ibuprofen | 0.5 g |
| chlorpheniramine maleate | 0.03 g |
| phosphoric acid | 0.1 g |
| con. glycerol | 2.6 g |
| hydrochloric acid | appropriate amount |

-continued

| | |
|---|---|
| sodium hydroxide | appropriate amount |
| sterile purified water | appropriate amount |
| total amount | 100 ml (pH 7) |

EXAMPLE 14

A nasal drop having the following formulation was prepared.

| | |
|---|---|
| enoxacin | 0.03 g |
| ibuprofen | 0.5 g |
| pyridoxine hydrochloride | 0.1 g |
| phosphoric acid | 0.1 g |
| con. glycerol | 2.6 g |
| hydrochloric acid | appropriate amount |
| sodium hydroxide | appropriate amount |
| sterile purified water | appropriate amount |
| total amount | 100 ml (pH 7) |

EXAMPLE 15

An eye drop having the following formulation was prepared.

| | |
|---|---|
| enoxacin | 0.25 g |
| 2-naphthoic acid | 0.2 g |
| naphazoline hydrochloride | 0.003 g |
| boric acid | 1.6 g |
| hydrochloric acid | appropriate amount |
| sodium hydroxide | appropriate amount |
| sterile purified water | appropriate amount |
| total amount | 100 ml (pH 6) |

EXAMPLE 16

An eye drop having the following formulation was prepared.

| | |
|---|---|
| enoxacin | 0.25 g |
| 2-naphthoic acid | 0.2 g |
| chlorpheniramine maleate | 0.03 g |
| boric acid | 1.6 g |
| hydrochloric acid | appropriate amount |
| sodium hydroxide | appropriate amount |
| sterile purified water | appropriate amount |
| total amount | 100 ml (pH 6) |

EXAMPLE 17

An eye drop having the following formulation was prepared.

| | |
|---|---|
| enoxacin | 0.25 g |
| 2-naphthoic acid | 0.2 g |
| pyridoxine hydrochloride | 0.1 g |
| boric acid | 1.6 g |
| hydrochloric acid | appropriate amount |

| | |
|---|---|
| sodium hydroxide | appropriate amount |
| sterile purified water | appropriate amount |
| total amount | 100 ml (pH 6) |

According to the solubilizing method of the present invention, the solubility of a pyridonecarboxylic acid compound and a salt thereof at near physiological pH can be increased, thereby making the production of an aqueous solution to be used as an eye drop, nasal drop, ear drop or the like possible.

This application is based on application No. 21807/1997 filed in Japan, the content of which is incorporated hereinto by reference.

What is claimed is:

1. A method for solubilizing a pyridonecarboxylic acid selected from the group consisting of lomefloxacin, norfloxacin, enoxacin, ofloxacin, ciprofloxacin, tosufloxacin, fleroxacin, cinoxacin, levofloxacin and sparfloxacin or a pharmacologically acceptable salt thereof, which comprises preparing an aqueous solution comprising said pyridonecarboxylic acid and an arylcarboxylic acid selected from the group consisting of pranoprofen, ibuprofen, bromfenac, 2-naphthoic acid, 2-naphthylacetic acid and 2-naphthoxyacetic acid or a pharmacologically acceptable salt thereof in a proportion of 0.001–50 parts by weight per part by weight of the pyridonecarboxylic acid.

2. An aqueous solution comprising a pyridonecarboxylic acid selected from the group consisting of lomefloxacin, norfloxacin, enoxacin, ofloxacin, ciprofloxacin, tosufloxacin, fleroxacin, cinoxacin, levofloxacin and sparfloxacin or a pharmacologically acceptable salt thereof in a concentration of 0.2–5.0 (w/v)%, and an arylcarboxylic acid selected from the group consisting of pranoprofen, ibuprofen, bromfenac, 2-naphthoic acid, 2-naphthylacetic acid and 2-naphthoxyacetic acid or a pharmacologically acceptable salt thereof in a proportion of 0.001–50 parts by weight per part by weight of the pyridonecarboxylic acid.

3. The solution of claim 2, which is an eye drop.

4. The solution of claim 2, which is a nasal drop.

5. The solution of claim 2, which is an ear drop.

6. An aqueous solution comprising at least a pyridonecarboxylic acid selected from the group consisting of lomefloxacin, norfloxacin, enoxacin, ofloxacin, ciprofloxacin, tosufloxacin, fleroxacin, cinoxacin, levofloxacin and sparfloxacin or a pharmacologically acceptable salt thereof in a concentration of 0.2–5.0 (w/v)%.

* * * * *